United States Patent
Domloge et al.

(10) Patent No.: US 9,962,329 B2
(45) Date of Patent: *May 8, 2018

(54) COSMETIC USE OF THE COMBINATION OF A CAROB GERM EXTRACT AND CAFFEINE AS A SLIMMING ACTIVE AGENT

(71) Applicant: ISP INVESTMENTS INC., Wilmington, DE (US)

(72) Inventors: Nouha Domloge, Valbonne (FR); Frederique Portolan, Valbonne (FR); Anne Clement, Paris (FR); Jean-Marie Botto, Garbejaire (FR)

(73) Assignee: ISP Investments, LLC, Wilmington, DE (US)

( * ) Notice: Subject to any disclaimer, the term of this patent is extended or adjusted under 35 U.S.C. 154(b) by 221 days.

This patent is subject to a terminal disclaimer.

(21) Appl. No.: 14/648,942

(22) PCT Filed: Dec. 10, 2013

(86) PCT No.: PCT/FR2013/053022
§ 371 (c)(1),
(2) Date: Jun. 2, 2015

(87) PCT Pub. No.: WO2014/091147
PCT Pub. Date: Jun. 19, 2014

(65) Prior Publication Data
US 2015/0306023 A1    Oct. 29, 2015

(30) Foreign Application Priority Data
Dec. 11, 2012   (FR) ..................... 12 03364

(51) Int. Cl.
| | | |
|---|---|---|
| A61K 8/97 | (2017.01) | |
| A61K 8/49 | (2006.01) | |
| A61K 8/64 | (2006.01) | |
| A61Q 19/06 | (2006.01) | |

(52) U.S. Cl.
CPC .............. *A61K 8/97* (2013.01); *A61K 8/4953* (2013.01); *A61K 8/645* (2013.01); *A61Q 19/06* (2013.01)

(58) Field of Classification Search
None
See application file for complete search history.

(56) References Cited

U.S. PATENT DOCUMENTS

| | | |
|---|---|---|
| 5,194,259 A | 3/1993 | Soudant et al. |
| 5,436,230 A | 7/1995 | Soudant et al. |
| 5,958,473 A | 9/1999 | Klinger et al. |
| 8,722,108 B2 | 5/2014 | Dal Farra et al. |
| 2005/0186290 A1 | 8/2005 | Cals-Grierson |
| 2008/0004283 A1 | 1/2008 | Landini et al. |
| 2012/0282198 A1 | 11/2012 | Dal Farra et al. |

FOREIGN PATENT DOCUMENTS

| | | |
|---|---|---|
| EP | 0689771 | 1/1996 |
| FR | 2609395 | 7/1988 |
| FR | 2669537 | 5/1992 |
| FR | 2671487 | 7/1992 |
| FR | 2858769 | 2/2005 |
| FR | 2859104 | 3/2005 |
| FR | 2867683 | 9/2005 |
| FR | 2879924 | 6/2006 |
| FR | 2887447 | 12/2006 |
| WO | 01/64177 | 9/2001 |
| WO | 2011/077017 | 6/2011 |

OTHER PUBLICATIONS

M. Hara-Chikuma et al.; "Progressive Adipocyte Hypertrophy in Aquaporin-7-deficient Mice: Adipocyte Glycerol Permeability as a Novel Regulator of Fat Accumulation"; The Journal of Biological Chemistry; vol. 280, No. 16; pp. 15493-15496 (Apr. 1, 2005).
J. Parrado et al.; "Production of a carob enzymatic extract: Potential use as a biofertilizer"; Bioresource Technology, Elsevier BV, GB; vol. 99, No. 7; pp. 2312-2318 (Feb. 8, 2008).
Osborne, T. B.; "Products of Hydrolysis of Vegetable Proteins", Chapter IX; Longmans, Green and Co., London; pp. 68-154 (1924).
International Search Report; International Application No. PCT/FR2013/053022 (dated Jun. 23, 2014).
BodyFit brochure, Feb. 2006, Sederma Inc., internet http://consumersguides.com/cellulite_cream_reviews/clinicals/Bodyfit.pdf, downloaded Aug. 24, 2017.

*Primary Examiner* — Susan Hoffman
(74) *Attorney, Agent, or Firm* — FisherBroyles, LLP; Susan M. Oiler

(57) ABSTRACT

Cosmetic methods for obtaining a slimming effect are disclosed. The methods include providing a composition containing a carob (*Ceratonia siliqua* L.) seed extract and caffeine or a derivative of caffeine as a slimming active agent and a physiologically acceptable medium, and topically applying the composition on at least a portion of the body or face. The topical application of the composition includes the application of an effective amount of the composition that increases the expression of aquaglyceroporins, increase lipolysis, promotes the elimination of lipids, reduces localized excess body fat, and/or attenuates the "orange peel" appearance of the skin.

18 Claims, 1 Drawing Sheet

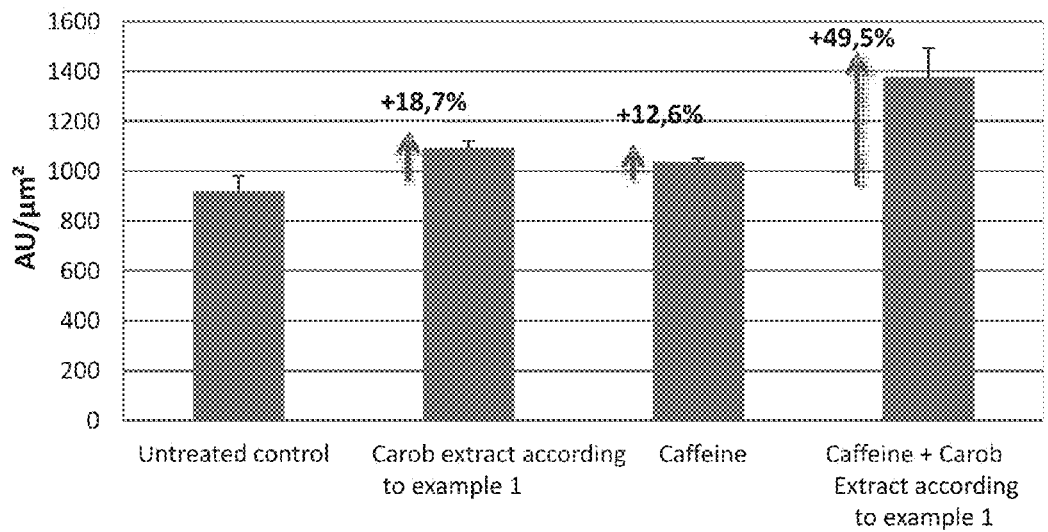
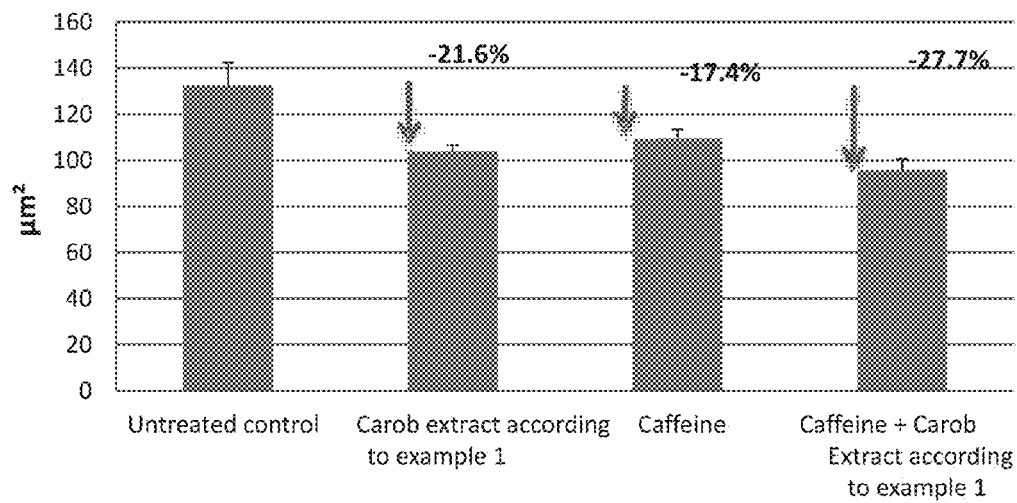

COSMETIC USE OF THE COMBINATION OF A CAROB GERM EXTRACT AND CAFFEINE AS A SLIMMING ACTIVE AGENT

CROSS-REFERENCE TO RELATED APPLICATIONS

This application is the national stage entry of International Patent Application No. PCT/FR2013/053022 filed on Dec. 10, 2013, which claims priority to French Patent Application No. 1203364 filed on Dec. 11, 2012.

FIELD OF THE INVENTION

This invention concerns the field of cosmetics and more specifically the field of cosmetic weight-loss methods. It relates to the cosmetic use of the combination of a carob germ extract (Ceratonia siliqua L.) and caffeine or a derivative thereof, as a slimming active agent. The invention also relates to the cosmetic use of the combination of a carob germ extract and caffeine or a derivative thereof for increasing the expression of aquaglyceroporins and promoting the elimination of triglycerides contained in adipocytes.

The invention also relates to a method of cosmetic care including the topical application, on at least a portion of the skin of the body or the face, of the association of a carob germ (Ceratonia siliqua L.) extract and caffeine or a derivative thereof, in a composition containing a physiologically acceptable medium, in order to obtain a weight-loss effect, and more specifically to reduce localized excess body fat.

BACKGROUND OF THE INVENTION

The subcutaneous adipose tissue is located at the hypodermis. It is a type of connective tissue where adipocytes are predominant, organized in lobes around 5 mm in diameter, separated by fine connective bridges. Each adipocyte contains a voluminous lipid vacuole containing essentially triglycerides and having a diameter that may range from 40 to 120 µm.

Adipose tissue may be considered to be a dynamic reservoir, constantly being renewed, balancing the dietary intake with the energy requirements of the body. Thus, adipocytes ensure the synthesis, accumulation and release of lipids. This process is dependent upon hormones such as insulin or leptin.

Lipid synthesis, or lipogenesis, originates with triglycerides of dietary origin and glucose. Conversely, the triglycerides stored in the adipocytes may be hydrolyzed, during lipolysis, to release fatty acids, glycerol and glycerol mono- and diesters.

The non-esterified fatty acids thus released may circulate in the blood and then be available for the energy requirements of other cells of the body, or be quickly reused by the adipocyte so as to generate, again, triglycerides by lipogenesis.

If a sustained imbalance occurs in the body promoting lipogenesis, the quantity of lipids stored in the adipocytes increases, leading to hyperplasia of the mass of body fat and more specifically to the appearance of localized excess body fat. In fact, in human adults, under the effect of sex hormones, the adipose tissue is distributed differently according to sex and forms the silhouette. Adipose tissue accumulates in the chest, on the hips, the buttocks and the thighs in women, and on the nape and shoulders in men. In addition, localized excess body fat is often associated with modifications in the skin, which develops a dimpled or "orange-peel" appearance. This localized excess body fat is currently considered to be unattractive, and people affected may want to improve the appearance of their skin and silhouette using cosmetic methods.

Numerous active agents having an action on lipolysis or lipogenesis, intended for slimming effect, have thus been identified. Among them, the following may be cited:

Xanthine bases (xanthine derivatives), such as theophylline, caffeine, theobromine (described in patents FR 2 609 395, FR 2 671 487), used for their action promoting the lipolytic activity of fat cells.

Synthetic peptides, such as the peptide of sequence Arg-Gly-Ser-NH2 (described in patent FR 2 858 769), or the peptide of sequence Pro-Leu-Asp-Thr-Ala-Lys-Val-Arg-Leu-Gln (described in patent FR 2 879 924) used for their action in the decoupling between coenzyme reoxidation and phosphorylation of ADP into ATP in the mitochondria.

Plant extracts, such as marine algae extract of the Palmaria or Rhodymenia genus (described in patent FR 2 887 447), gingko biloba extracts (see patent FR 2 669 537), or soy flavones or isoflavones (described in patent WO 01/64177).

However, these products generally have moderate or limited efficacy over time. It is therefore important to provide new active cosmetic agents having remarkable efficacy as slimming active agents.

The solution to the technical problem addressed lies in the cosmetic use of the association of a carob germ extract and caffeine or a derivative thereof. The inventors have indeed demonstrated that a carob germ extract acts on aquaglyceroporins, thereby promoting the transport of glycerol released during lipolysis, from the adipocyte. The association of this extract with caffeine, or derivatives thereof, the latter already being known to increase lipolysis, makes it possible to obtain a slimming active agent having remarkable properties.

Aquaporins are a class of transmembrane proteins carrying water and small molecules in solution, between the cells and the internal medium. Aquaporins may be classified into two distinct sub-groups: aquaporins enabling only the transport of water, and aquaglyceroporins which enable, in addition to the transport of water, the transport of glycerol.

In this second sub-group, aquaglyceroporin 7 was identified in the membrane of human adipocytes and plays an important role in the metabolism of reserve fats (Mariko Hara-Chikuma et al. Progressive adipocyte hypertrophicity in aquaporin-7 deficient mice, J. Biol. Chem., vol. 280, no. 16, Apr. 22, 2005).

The particular properties of aquaglyceroporins therefore makes them beneficial biological targets for promoting the elimination of lipids contained in the adipocytes.

"Elimination of lipids" refers to the phenomenon of lipolysis leading to the export of glycerol from the adipocyte cell.

The invention and the resulting advantages will be better understood upon reading the description.

BRIEF DESCRIPTION OF THE DRAWINGS

FIG. 1 is a graph of immuno-detection data of aquaglyceroporin 7 in 3T3-L1 cells.

FIG. 2 is a graph of the quantification of the size of lipid droplets in 3T3-L1 cells.

DESCRIPTION OF THE INVENTION

This invention first relates to the cosmetic use of the association of a carob germ extract (*Ceratonia siliqua* L.) and caffeine or a derivative thereof, as a slimming active agent.

The association of the carob germ extract and caffeine or a derivative thereof, used according to the invention, provides in particular the following advantages:
    it increases lipolysis,
    it increases the expression of aquaglyceroporins,
    it promotes the elimination of lipids and the export of glycerol from the adipocytes,
    it reduces localized excess body fat,
    it attenuates the "orange peel" appearance of the skin.

Thus, "slimming active agent" in the sense of this invention refers to the association of a carob germ extract and caffeine or a derivative thereof, used to reduce excess localized body fat, considered to be unattractive and often associated with a dimpled or "orange peel" appearance of the skin.

Carob seed (plant of the *Ceratonia* genus), and more specifically the endosperm fraction of said seed, is widely used for its rich galactomannan content in the food industry under the name "carob gum". The germ is the portion of the seed highest in protein and can easily be isolated.

A carob germ protein extract, obtained by enzymatic hydrolysis, has already been described (J. Parrado et al., Bioresource Technology 99, 2008). Nevertheless, this extract has too high a concentration of phytohormones, an endocrine disrupter, to be used in cosmetics.

To carry out the invention, any extraction or purification method known to a person skilled in the art may be used, such as, for example, the method described in the European patent application EP 0 689 771.

"Peptide extract" refers to a mixture of compounds predominantly represented by peptide compounds, in solution in a large volume of water or other solvents, polar or a mixture of these solvents.

"Peptide compounds" refers to protein fragments and peptides present in the peptide extract according to the invention.

"Topical application" refers to the application or spreading of the active agent according to the invention, or a composition containing it, on the surface of the skin or a mucous membrane.

"Physiologically acceptable" refers to any compound suitable for coming into contact with the skin or a mucous membrane without causing reactions of toxicity or intolerance.

"Excess localized body fat" refers to a hypertrophied area of the subcutaneous adipose tissue, which may have an "orange peel" appearance.

In the description below, the terms "active agent for slimming effect" and "association of a carob germ extract and caffeine or a derivative thereof" will be used interchangeably.

The carob germ extract according to the invention may be obtained by extracting proteins of plant origin, followed by a controlled hydrolysis that releases the biologically active peptide compounds.

The use of peptide extracts, and in particular peptide extracts of low molecular weight, has numerous advantages in cosmetics. Aside from the fact of generating peptide compounds that did not previously exist in the starting protein mixture, hydrolysis and purification make it possible to obtain mixtures with greater stability, compositions that are easier to reproduce and not causing allergic reactions in cosmetics.

To carry out the extraction, carob seed germ (plant of the *Ceratonia* genus) is used. Any extraction or purification method known to a person skilled in the art may be used to prepare the extract according to the invention. For example, controlled hydrolysis makes it possible to release peptide compounds. It is possible, but unnecessary in order to carry out the invention, either to extract the proteins concerned and then hydrolyze them, or to perform the hydrolysis on a raw extract and then to purify the peptide compounds.

In a first step, the germ contained in the seeds is ground so as to obtain a powder or flour. The powder thus obtained may first be treated by a cellulase in order to promote the elimination of sugars, and in particular insoluble polysaccharides.

Then, the extraction of the proteins of the germ is performed according to the modified conventional process (Osborne, T. B., The Vegetable Proteins, 2nd Edition. Longmans, Green and Co., London, 1924); the ground carob germ is suspended in an alkaline solution containing an insoluble adsorbent polyvinylpolypyrrolidone (PVPP) product (0.01-20%); in fact, it is known that subsequent hydrolyses and purifications are facilitated by this means. In particular, the concentration of phenol substances interacting with the proteins is clearly reduced. The proteins can then be precipitated by varying the ionic strength or by acidifying the medium, thereby making it possible to eliminate the soluble components and the nucleic acids. The precipitate is then washed with an organic solvent such as, for example, ethanol or methanol, then the solvent is evaporated by vacuum drying. The protein-rich precipitate is placed in solution in water or another solvent and thus constitutes a more purified form of the extract.

The extraction may also be performed in a neutral or acid medium, still in the presence of polyvinylpolypyrrolidone. After a filtration step, the precipitation step is then carried out with a conventional precipitation agent such as salts (sodium chloride, ammonium sulfate) or an organic solvent (alcohol, acetone). The precipitate obtained may be separated from the precipitation agents by dialysis after being placed in solution in water or another solvent.

The soluble fraction, containing proteins, carbohydrates and possibly fats, is collected after the centrifugation and filtration step. This raw solution is then hydrolyzed under controlled conditions in order to generate soluble peptides. Hydrolysis is defined as being a chemical reaction involving the cleaving of a molecule by water, said reaction being capable of being produced in a neutral, acid or basic medium. According to the invention, hydrolysis is performed chemically and/or advantageously by proteolytic enzymes among which plant-based endoproteases may be cited (papain, bromelin, ficain).

According to a first embodiment of the invention, the slimming active agent includes the hydrolyzed carob germ extract obtained in this step.

For the same reasons as above, i.e. the elimination of polyphenol substances, a quantity of polyvinylpolypyrrolidone may be added to the reaction medium during this step of controlled hydrolysis. The extract obtained may again be purified in order to select the low-molecular-weight peptide compounds. Fractionation may advantageously be performed by ultra-filtration and/or by a chromatographic method.

Then a phase of dilution in water or in any mixture of solvents containing water is performed. Thus, according to an advantageous embodiment of the invention, the carob germ extract according to the invention is advantageously diluted in one or more physiologically acceptable solvents, such as water, glycerol, ethanol, propanediol, butylene glycol, dipropylene glycol, ethoxylated or propoxylated diglycols, cyclic polyols or any mixture of these solvents. The diluted carob germ extract is then sterilized by ultra-filtration.

After this dilution, a peptide extract is obtained, which is characterized by a dry weight of 2 to 5 g/kg, a peptide compound concentration of 1 to 10 g/l, preferably 1.5 to 3.5 g/l, a sugar concentration of 0.05 to 1 g/l, preferably 0.1 to 0.3 g/l and a polyphenol concentration of less than 1% with respect to the dry weight.

Thus, according to an advantageous embodiment of the invention, the carob germ extract has a dry weight of 2.5 g/kg and contains between 1.5 and 3.5 g/l of peptide compounds.

The physicochemical characteristics and the protein and peptide compound content of the extract obtained according to the invention are qualitatively and quantitatively analyzed, according to conventional techniques well known to a person skilled in the art.

The extract obtained is comprised of peptides having a molecular weight below 5 kDa and is characterized by a sugar concentration below 15% and a polyphenol concentration below 1% with respect to the dry weight.

Thus, according to an advantageous embodiment of the invention, the carob germ extract is a peptide extract in which the peptide compounds have a molecular weight below 5 kDa.

Caffeine is a heterocyclic molecule of plant origin forming part of the group of purine bases, and more specifically methylxanthines.

The lipolytic effect of caffeine has been demonstrated by numerous in vitro and in vivo studies. Caffeine promotes the accumulation of cyclic AMP which itself activates triglyceride-lipase, responsible in the adipocyte for the transformation of triglycerides into glycerol and free fatty acids.

Caffeine derivatives have been developed to improve the solubility, cutaneous penetration, bioavailability or efficacy of caffeine. Caffeine derivatives may be chosen from caffeine acid derivatives, caffeine salts, and more specifically caffeine carboxylate metal salts.

This invention also relates to the use of the association of an extract of carob germ and caffeine or a derivative thereof in order to increase the expression of aquaglyceroporins and more specifically aquaglyceroporin 7.

The characteristic molecular activity of the invention is defined in vitro by the capacity of the slimming active agent to increase the expression of aquaglyceroporins, either by increasing the protein synthesis of aquaglyceroporins (by direct or indirect modulation of the gene expression of aquaglyceroporins), or by other biological processes such as the stabilization of the aquaglyceroporin protein or the stabilization of messenger RNA transcripts.

Preferably, according to this invention, aquaglyceroporin is aquaglyceroporin 7.

This invention also relates to the use of the association of an extract of carob germ and caffeine or a derivative thereof in order to increase lipolysis and promote the elimination of lipids and the export of glycerol from the adipocytes.

The characteristic biological activity of the invention is defined in vitro by the capacity of the slimming active agent to reduce the size and number of lipid droplets in the adipocytes.

This invention also relates to a cosmetic care method including the topical application, on at least a portion of the skin of the body or face, of the association of a carob germ extract (*Ceratonia siliqua* L.) and caffeine or a derivative thereof, in a composition containing a physiologically acceptable medium, in order to obtain a weight-loss effect, and more specifically in order to reduce excess localized body fat.

This invention also relates to a cosmetic care method including the topical application, on at least a portion of the skin of the body or face, of the association of a carob germ extract (*Ceratonia siliqua* L.) and caffeine or a derivative thereof, in a composition containing a physiologically acceptable medium, in order to attenuate the "orange peel" appearance of the skin.

Advantageously, the carob germ extract is present in a concentration of between 0.0001% and 20% of the total weight of the composition, and preferably in a concentration of between 0.05% and 5% of the total weight of the composition, in a physiologically acceptable medium.

Advantageously, the caffeine, or a derivative thereof, is present in a concentration of between 0.0001% and 20% of the total weight of the composition, and preferably in a concentration of between 0.05% and 5% of the total weight of the composition, in a physiologically acceptable medium.

According to another advantageous embodiment of the invention, the carob germ extract may be encapsulated or included in a cosmetic vector such as a liposome or any other microcapsule used in the field of cosmetics or adsorbed on powdery organic polymers, mineral supports such as talcs and bentonites.

The compositions for implementation of the invention may in particular be in the form of an aqueous, hydroalcoholic or oily solution; and oil-in-water emulsion, a water-in-oil emulsion or multiple emulsions; they may also be in the form of suspensions, or powders, suitable for application on the skin, mucous membranes, lips and/or hair.

These compositions may be more or less fluid and have the appearance of a cream, a lotion, a milk, a serum, a pomade, a gel, a paste or a foam. They may also be in solid form such as a stick or be applied on the skin in the form of aerosol.

These compositions may also include any additive commonly used in the field of application envisaged, as well as the adjuvants necessary for their formulation, such as solvents, thickeners, diluents, antioxidants, coloring agents, sunscreens, self-tanning agents, pigments, fillers, preservatives, fragrances, odor absorbers, cosmetic or pharmaceutical active agents, essential oils, vitamins, essential fatty acids, surfactants, film-forming polymers, and so on.

In every case, a person skilled in the art will ensure that said adjuvants as well as the proportions thereof are chosen so as not to interfere with the desired advantageous properties of the composition of the invention. These adjuvants may, for example, correspond to 0.01 to 20% of the total weight of the composition. When the composition of the invention is an emulsion, the fatty phase may represent 5 to 80% by weight and preferably 5 to 50% by weight with respect to the total weight of the composition. The emulsifiers and co-emulsifiers used in the composition will be chosen from those conventionally used in the field considered. For example, they may be used in a proportion ranging from 0.3 to 30% by weight, with respect to the total weight of the composition.

Advantageously, the composition capable of being used for the invention may include, in addition to the slimming active agent according to the invention, at least one other active agent having cosmetic effects that are similar and/or complementary to those of the invention. According to the invention, this active agent will be defined as an "additional active agent".

For example, the additional active agent(s) may be chosen from: anti-aging, toning, lightening, hydrating, draining, and microcirculation-promoting agents, pharmaceutical, exfoliating, scrubbing, extracellular matrix-stimulating, energy metabolism-activating, antibacterial, antifungal, calming, anti-free radical, anti-UV and anti-acne agents, anti-inflammatory agents, anesthetics, warming agents, cooling agents and weight-loss agents.

Such additional agents may be chosen from the groups including:
  vitamin A and in particular retinoic acid, retinol, retinol propionate, retinol palmitate,
  vitamin B3 and more specifically niacinamide, tocopherol nicotinate,
  vitamin B5, vitamin B6, vitamin B12,
  vitamin C, in particular ascorbic acid, ascorbyl glucoside, ascorbyl tetrapalmitate, magnesium and sodium ascorbyl phosphate,
  vitamins E, F, H, K, PP, coenzyme Q10,
  metalloproteinase inhibitors, a TIMP activator,
  DHEA, precursors and derivatives thereof,
  amino acids such as arginine, ornithine, hydroxypropline, hydroxyproline dipalmate, palmitoylglycine, hydroxylysine, methionine and derivatives thereof, N-acyl amino acid compounds,
  natural or synthetic peptides, including di-, tri-, tetra-, penta- and hexapeptides and the lipophilic derivatives thereof, isomers and complexed with other species such as a metal ion (e.g. copper, zinc, manganese, magnesium, and others). For example, the peptides commercially known under the names MATRIXYL®, ARGIRELINE®, COLLAXYL™, PEPTIDE VINCI 02™, CHRONOGEN™ LAMINIXYL IS™, PEPTIDE Q10™
  plant-based peptide extracts such as extracts of soy, spelt, grapevine, rapeseed, linseed, rice, corn, pea,
  yeast extracts, *Artemia Salina* extracts,
  dehydroacetic acid (DHA),
  phytosterols of synthetic or natural origin,
  salicylic acid and derivatives thereof, alpha- and beta-hydroxyacids,
  amino sugars, glucosamine, D-glucosamine, N-acetyl-glucosamine, N-acetyl-D-glycosamine, mannosamine, N-acetyl mannosamine, galactosamine, N-acetyl galactosamine,
  extracts of polyphenols, isoflavones, flavonoids, such as grape extracts, pine extracts and olive extracts,
  lipids such as ceramides or phospholipids, oils of animal origin, such as squalene or squalane; plant oils, such as sweet almond, copra, ricin, jojoba, olive, rapeseed, peanut, sunflower, wheat germ, corn germ, soy, cottonseed, alfalfa, poppy, winter squash, evening primrose, millet, barley, rye, safflower, passion fruit, hazelnut, palm, apricot seed, avocado, and calendula oil; ethoxylated plant oils, and shea butter,
  all UV screens and sunscreens.

Especially advantageously, the invention may include at least one additional active agent known for its slimming action, inhibiting lipogenesis or stimulating lipolysis, such as: cyclic AMP and derivatives thereof, adenylate cyclase enzyme activating agents and phosphodiesterase enzyme inhibiting agents, *centalla asiatica* extract, asiaticoside and asiatic acid, methyl xanthines, thein, theophylline, theobromine, forskoline, esculin and esculoside, ACE inhibitors, the peptide Val-Trp, neuropeptide Y inhibitors, enkephalin, *gingko biloba* extract, dioscorea extract, rutin, verba mate extract, guarana extract, oligosaccharides, polysaccharides, carnitine, ivy extract, rockweed extract, hydrolyzed *Prunella vulgaris* extract, hydrolyzed *Celosia cristata* extract, *Anogeissus leiocarpus* extract, *Manihot utilissima* leaf extract, palmitoylcarnitine, carnosine, taurine, elderberry extract, algae extracts such as *Palmaria Palmata* extract, the synthetic peptide of sequence Arg-Gly-Ser-NH$_2$, sold under the name ATPEPTIDE™, the synthetic peptide of sequence Pro-Leu-Asp-Thr-Ala-Lys-Val-Arg-Leu-Gln sold under the name ATPEPTIDE™.

The composition capable of being used according to the invention may be applied by any suitable route, in particular oral or external topical, and the formulation of the compositions will be adapted by a person skilled in the art.

Advantageously, the compositions according to the invention are in a form suitable for topical application. These compositions must therefore contain a physiologically acceptable medium, i.e. compatible with the skin and skin appendages, and cover all cosmetic forms.

It is obvious that the invention concerns mammals in general, and more specifically human beings.

Specific embodiments of this cosmetic treatment method also result from the above description. Other advantages and features of the invention will be more apparent upon reading the examples provided for illustrative and non-limiting purposes.

FIG. 1: Immuno-detection of aquaglyceroporin 7 in 3T3-L1 cells.

FIG. 2: Quantification of the size of lipid droplets in 3T3-L1 cells.

EXAMPLE 1: PREPARATION OF A CAROB PEPTIDE EXTRACT (*CERATONIA SILIQUA* L.)

Carob germ (*Ceratonia siliqua* L.) in powder form is placed in solution in 70 volumes of water and the pH is adjusted to a value of between 4.5 and 5.5.

To eliminate insoluble sugars, hydrolysis with a cellulase is performed. For this, 2% CELLUCLAST® CL enzyme (Novozymes) and 2% POLYCLAR® 10 (polyvinylpyrrolidone—PVPP—insoluble) are added to the reaction medium. The reaction medium is then heated for two hours at 50° C. then deactivated for one hour at 80° C. A filtration step makes it possible to separate the carbohydrate-rich filtrate so as to preserve only the solid residue.

The latter is characterized by a protein content of between 45 and 50% and a sugar content of between 20 and 30%.

The dry residue thus obtained is placed in solution in 100 volumes of water in the presence of 2% POLYCLAR® 10 polyvinylpyrrolidone. The mixture is adjusted to a pH of between 8.0 and 8.5 with a 2 M aqueous soda solution.

To improve the extraction of proteins, a first hydrolysis is performed with 2% ALCALASE® enzymes (Novozymes). The hydrolysis is obtained after 2 hours, under stirring, at 55° C. The enzyme is inactivated by heating the solution at 80° C. for 2 hours. After deactivation, the reaction mixture is filtered and the filtrate is collected. This is the intermediate carob germ protein extract.

At this stage in the preparation, the peptide and protein compounds of said filtrate are characterized by electrophoresis on polyacrylamide gel (NUPAGE® Bis-Tris Precast gels, Invitrogen). For this, the filtrate is heated at 70° C. for 10 minutes under denaturing reducing conditions in a NUPAGE® LDS sample preparation buffer. A NUPAGE® antioxidant solution is added to the interior vat (cathode) in order to prevent the reduced proteins from being reoxidized during electrophoresis. The migration of proteins is performed in NUPAGE® MES migration buffer in the presence of a molecular weight standard (SeeBlue Plus2). The staining of the proteins is performed with COOMASSIE™ Blue R-250. The protein profile thus obtained shows that the peptide and protein compounds of the filtrate have molecular weights between 50 and 10 kDa.

The intermediate carob germ protein extract is then placed in solution in 100 volumes of water in the presence of 2% POLYCLAR® 10 polyvinylpyrrolidone. The mixture is adjusted to a pH of between 4 and 5 with a 1 M aqueous hydrochloric acid solution.

A step of hydrolysis of the proteins is then performed with an endoprotease. For this, 2% bromelain is added to the reaction medium. The hydrolysis is obtained after 2 hours of stirring at 50° C. The enzyme is inactivated by heating the solution at 80° C. for 2 hours.

The purification of the extract thus obtained is continued by successive filtrations with Seitz-Orion filter-plates of decreasing porosity (to 0.2 µm) in order to obtain a clear, bright solution. After this filtration series, the carob germ extract is characterized by a dry weight between 20 and 25 g/kg, a protein content between 10 and 15 g/l, a sugar content between 5 and 6 g/l, an amino acid content between 1 and 2 g/l and a total polyphenol content between 0.5 and 1 g/l. The proteins are assayed by a specific colorimetric method (Lowry method).

The protein profile of this extract is analyzed by electrophoresis gel. Under the same conditions as described above, 2 large families of proteins are observed: the first family, in the minority, corresponds to proteins having a molecular weight of 25 to 20 kDa and the second family, very much in the majority, corresponds to proteins having a molecular weight below 5 kDa.

This extract is then purified by eliminating the proteins having a molecular weight above 5 kDa by tangential flow filtrations steps. For this, the carob germ extract is pumped under pressure through a PELLICON® substrate equipped with a PELLICON® 2 Biomax cassette 30 kDa. The first filtrate obtained is recovered so as to be filtered again through another PELLICON® 2 Biomax 5 kDa cassette.

At the end of the purification, a clear, bright, yellow-orange carob germ extract is obtained. It is characterized by a dry weight between 8 and 9 g/kg, a protein content between 6 and 7 g/l, a sugar content between 0.3 and 0.5 g/l and a total polyphenol content below 0.1 g/l.

Then, a dilution phase is performed in a water-glycerol mixture in order to obtain a peptide extract characterized by a dry weight of 2 to 5 g/kg, and preferably 2.5 g/kg, a peptide compound concentration of 1.5 to 3.5 g/l, a sugar concentration of 0.1 to 0.3 g/l (below 15%) and a polyphenol concentration below 1%.

This purified and diluted extract corresponds to the carob germ peptide extract according to the invention. It is characterized by the fact that the peptide compounds have a molecular weight below 5 kDa, with a polyphenol content below 1%.

This solution is then analyzed by high-pressure liquid chromatography with an HP1100 apparatus controlled by ChemStation software. The column used during elution of the carob extract is NUCLEOSIL® 300-5 C4 MPN (125×4 mn). This column makes it possible to chromatographically analyze proteins having molecular weights of 0.2 to 25 kDa (according to a suitable solvent gradient). Under these chromatographic conditions, a plurality of peptide fractions were isolated. These various fractions were analyzed by mass spectrometry in order to identify their molecular peaks. The amino acid composition was also determined. It is obtained after acid hydrolysis and identification by high-pressure liquid chromatography by means of pre-differentiation with PICT (phenyl-isothiocyanate).

EXAMPLE 2: EVALUATION OF THE EXPRESSION OF AQUAGLYCEROPORIN 7

The objective of this study is to determine the influence of the association of the carob extract according to example 1 and caffeine, on the expression of aquaglyceroporin 7 in differentiated 3T3-L1 adipocyte cells.

Protocol:

Culture and Differentiation of 3T3-L1 Cells:

3T3-L1 adipocyte cells are cultivated in a DMEM medium with 4.5 g/l glucose, 2 mM glutamine and 10% fetal bovine serum.

Two days after the cell confluence phase, the differentiation of 3T3-L1 cells into adipocytes is induced by adding a solution of 0.5 mM of IBMX, 1 µM of dexamethasone and 10 µg/ml of insulin (Sigma, St. Louis, Mo., USA) in the culture medium for 3 days. Then, only the insulin is kept for 3 to 4 days of additional culture. The cells are then kept in culture, in a standard medium, for another 3 days.

Treatment:

The treatment is performed from the start of the differentiation induction phase by a daily application, for 12 days, of 1×PBS (Lonza, Rockland, Me., USA) for the untreated control, carob germ extract with a dry weight of 2.5 g/kg as obtained in example 1, diluted to 1% in PBS, or carob germ extract as obtained in example 1, diluted to 1% in PBS and to which 2 mM of caffeine is added for the last 5 hours of the treatment. A 5-hour treatment with 2 mM of caffeine was also performed.

Immunolabeling of Aquaglyceroporin 7:

The cells are washed 3 times with 1×PBS (Lonza, Rockland, Me., USA) and fixed with 3.7% formaldehyde (Sigma Aldrich, USA) for 10 minutes at ambient temperature. The cell membranes are permeabilized with acetone for 4 minutes at −20° C. The non-specific sites are saturated with 3% bovine serum albumin (Sigma-Aldrich, Steihheim, Germany) for 15 minutes. The primary antibody (rabbit polyclonal anti-aquaglyceroporin 7 (Santa Cruz Biotechnology) diluted to 1/100) is applied for 1.5 hour. After multiple rinses, a second antibody, coupled to the Alexa Fluor 488 probe (Alexa Fluor 488 donkey anti-rabbit (Invitrogen, Fisher) diluted to 1/1000) is applied for 1 hour. The slides are then mounted in the Fluoromount G (Electron Microscopy Science, Hatfield, UK).

The cells are examined with a Nikon Eclipse 80i microscope, with a 40× objective, and photographs are taken with the Nikon Digital DXM1200C camera.

Three images for each condition are analyzed using the Image-Pro Analyzer 6.3 software. The sum of light intensities is adjusted with respect to the culture surface (McMullen et al., 2010).

The statistical analysis uses a t-Student test for unpaired data, in which $P<0.05$ is considered to be significant; $P<0.1$ is considered to be very significant and $P<0.005$ is considered to be highly significant.

Results:

The microscopic observations show an insignificant 12.6% increase in fluorescence in differentiated 3T3-L1 cells treated with caffeine, with respect to the untreated control. A significant 18.7% increase in fluorescence is observed in cells treated with the 1% carob extract according to example 1, with respect to the untreated control. The quantitative analyses finally show a very significant 49.5% increase in fluorescence in the cells with respect to the untreated control, as is shown in FIG. 1.

Conclusions:

The association of the carob extract according to example 1 and caffeine causes a very significant increase in the expression of aquaglyceroporin 7 in differentiated 3T3-L1 adipocyte cells. Caffeine very substantially potentiates the effect of the 1% carob extract according to example 1.

EXAMPLE 3: EVALUATION OF LIPID DROPLETS CONTAINED IN ADIPOCYTES

The objective of this study is to measure the influence of the association of the carob extract according to example 1 and caffeine, on the size and number of lipid droplets contained in the differentiated 3T3-L1 adipocyte cells.

Protocol:

The culture, the differentiation of 3T3-L1 cells, then the treatment with the compounds to be tested are performed as in example 2.

Detection of Lipids by Nile Red:

The lipid detection is performed using Nile Red fluorescent stain, a phenoxazone that intensely labels the intracellular lipids.

The color of the fluorescence observed is directly dependent upon the hydrophobicity of the surrounding medium. This specific property of Nile Red makes it possible to differentiate neutral lipids, labeled in gold-yellow, from phospholipids, labeled in red.

The cells are fixed with a 3.7% formaldehyde solution for 10 minutes, then labeled by a solution of 100 nM Nile Red in PBS for 10 minutes, and finally rinsed in PBS.

The cells are examined with the fluorescence microscope. The quantification and statistical analysis are performed as in example 2.

Results:

The intensity of the Nile Red labeling, the size and the number of droplets in the differentiated 3T3-L1 cells treated with the 1% carob extract according to example 1, 2 mM of caffeine, and the association of the carob extract according to example 1 and caffeine, are reduced with respect to the untreated cells.

Concerning the association of the carob extract according to example 1 and caffeine, the quantitative analyses show a significant 42.78% reduction in the intensity of the labeling, a 27.7% reduction in the size of the droplets and a significant 33% reduction in the number of droplets with respect to the untreated cells. The quantification of the intensity of the staining, the size and the volume of the lipid droplets is illustrated in tables 1, 2 and 3. The quantification of the lipid droplet size is illustrated by FIG. 2.

TABLE 1

Intensity of the Nile Red labeling

| | Ratio (Pixels/$\mu m^2$) | % reduction | Standard deviation | t-Student test |
|---|---|---|---|---|
| Untreated control | 288.10 | | 31.22 | |
| 1% carob extract according to example 1 | 185.44 | −35.63 | 11.76 | significant |
| Caffeine | 180.47 | −37.36 | 9.22 | significant |
| Association of carob extract according to example 1 and caffeine 2 mM | 164.85 | −42.78 | 19.47 | significant |

TABLE 2

Evaluation of the droplet size

| | Average droplet size ($\mu m^2$) | % reduction | Standard deviation | t-Student Test |
|---|---|---|---|---|
| Untreated control | 132.65 | | 9.76 | |
| 1% carob extract according to example 1 | 104.01 | −21.60 | 2.47 | Significant |
| Caffeine | 109.55 | −17.40 | 3.75 | Significant |
| Association of carob extract according to example 1 and caffeine 2 mM | 95.92 | −27.7 | 4.74 | Insignificant |

TABLE 3

Evaluation of the number of droplets

| | Number of droplets | % reduction | Standard deviation | t-Student Test |
|---|---|---|---|---|
| Untreated control | 266 | | 29.00 | |
| 1% carob extract according to example 1 | 189 | −29 | 20 | significant |
| Caffeine | 219 | −18 | 13 | insignificant |
| Association of carob extract according to example 1 and caffeine 2 mM | 178 | −33 | 22 | significant |

Conclusion:

The association of the carob extract according to example 1 and caffeine causes a significant reduction in the size and the number of lipid droplets in differentiated 3T3-L1 adipocyte cells.

EXAMPLE 4: CLINICAL EVALUATION NO. 1 OF THE WEIGHT-LOSS EFFECT OF THE ASSOCIATION OF CAROB EXTRACT ACCORDING TO EXAMPLE 1 AND CAFFEINE

The objective of this study is to evaluate the weight-loss effect of the association of the carob extract according to example 1 and caffeine, in humans, by centimeter measurements.

Protocol:

A clinical study was conducted on 39 volunteers between 34 and 63 years of age (mean age: 52 years) with a twice-daily application on the different areas to be tested (waist, belly, hips, buttocks, thighs) for a period of 28 days.

The product tested is a standard cosmetic composition containing 2% caffeine and 2% carob extract according to example 1.

The efficacy is evaluated by comparing measurements at T0 and at T28 days, each volunteer being his or her own control.

Results:

Under the experimental conditions, after 28 days of application, a significant mean reduction in centimeter measurements is observed on the thighs (mean −0.8 cm), on the waist (mean −0.6 cm) and on the belly (mean −0.9 cm).

The data series has a normal distribution. The statistical analysis uses a t-Student test for paired data, in which $P<0.05$ is considered to be significant and noted *.

TABLE 4

|  | T0 | T1 month | Mean variation (T0-T1 month) | P significant if p < 0.05 | % of subjects responding | Variation in best third (cm) | % of subjects responding on at least one area |
|---|---|---|---|---|---|---|---|
| Treated thigh | 57.16 | 56.19 | −0.8* | $3.16^{E-08}$ | 69% | −1.48 | 88% |
| Control thigh | 57.13 | 56.95 |  |  |  |  |  |
| Belly (cm) | 94.77 | 93.84 | −0.9* | $6.03^{E-05}$ | 62% | −2.05 |  |
| Waist (cm) | 80.75 | 80.19 | −0.6* | $1.56^{E-02}$ | 59% | −1.50 |  |

Conclusion:

The twice-daily application of the association of the carob extract according to example 1 and 2% caffeine for 1 month enables significant slimming of the thighs, the waist and the belly.

EXAMPLE 5: CLINICAL EVALUATION NO. 2 OF THE WEIGHT-LOSS EFFECT OF THE ASSOCIATION OF THE CAROB EXTRACT ACCORDING TO EXAMPLE 1 AND CAFFEINE

The objective of this study is to evaluate the weight-loss effect of the association of the carob extract according to example 1 and caffeine, in humans, by centimeter measurements.

Protocol:

A clinical study was conducted on 26 volunteers between 30 and 65 years of age (mean age: 43.7 years) with a twice-daily application on the different areas to be tested (waist, belly, hips, buttocks, thighs) for a period of 28 days.

The product tested is a standard cosmetic composition containing 2% caffeine and 2% carob extract according to example 1.

The efficacy is evaluated by comparing measurements at T0 and at T28 days, each volunteer being his or her own control.

Results:

Under the experimental conditions, after 28 days of application, a significant mean reduction of 2.2 cm of the circumference of the abdomen, a significant mean reduction of 1.2 cm of the upper circumference of the thigh, and a significant mean reduction in the volume of the trunks of the thighs are observed.

The data series has a normal distribution. The statistical analysis uses a t-Student test for paired data, in which P<0.05 is considered to be significant.

In addition, a questionnaire made it possible to establish that the majority of volunteers estimated that the treated areas were smoother and firmer and that the "orange peel" appearance was attenuated.

Conclusion:

The twice-daily application of the association of the carob extract according to example 1 and 2% caffeine for 1 month enables significant thinning of the thighs and belly, as well as an attenuation of the "orange peel" appearance.

EXAMPLE 6: PREPARATION OF COMPOSITIONS

1 Slimming cream 1

| Phase | Component | Weight % |
|---|---|---|
| A | Purified water | 38.84 |
| A | Methylpropane diol | 3.00 |
| A | Glycereth-26 | 3.00 |
| B | Glycerin 100% veg. | 2.00 |
| B | Standard xanthan gum | 0.3 |
| C | Isododecane | 15.00 |
| C | DC 1503 Fluid | 3.0 |
| C | Tocopherol acetate | 0.5 |
| D | PEMULEN ® TR1 emulsifier | 0.5 |
| D | SYNTHALEN ® K synthetic polymer | 0.3 |
| E | NA 4 EDTA | 0.1 |
| E | L Arginine | 0.2 |
| E | Purified water | 1.4 |
| F | Salicylic acid | 0.4 |
| F | 96% alcohol of agricultural origin | 10.00 |
| G | purified water | 4.7 |
| G | Sodium hydroxide | 0.3 |
| H | PF grapefruit E 9509056/07 | 0.3 |
| I | Purified water | 8.58 |
| J | Caffeine | 2.0 |
| K | Sol. Col. FDC blue N1 0.1% without preservative | 0.640 |
| K | Sol. Col. FDC yellow 5 0.1% in MP DIOL | 0.440 |
| L | Bodyfit | 2.5 |
| L | Carob extract according to example 1 | 2.00 |

2 Slimming cream 2

| Phase | Component | Weight % |
|---|---|---|
| A | Purified water | 49.615 |
| A | Sodium hydroxide | 0.110 |
| A | Methylpropane diol | 4.00 |
| B | Salicylic acid | 0.4 |
| C | Caffeine | 1.5 |
| D | NA 4 EDTA | 0.1 |
| E | SYNTHALEN ® K synthetic polymer | 1.0 |
| F | Cetyl alcohol 20 OE | 1.0 |
| F | Coco-caprylate caprate | 9.00 |
| F | Cetyl alcohol | 2.00 |
| F | Shea butter 100% veg. | 2.00 |
| F | Beeswax 100% natural | 2.00 |
| F | Tocopherol acetate | 0.5 |
| F | Stearyl alcohol OV | 1.00 |
| F | Dimethicone 20 CST | 2.00 |
| G | Sodium hydroxide | 0.350 |
| G | Purified water | 2.00 |
| H | Dextran sulfate | 0.5 |
| H | Carob extract according to example 1 | 2.00 |
| H | Purified water | 3.00 |
| I | Rutin | 0.05 |

-continued

2 Slimming cream 2

| Phase | Component | Weight % |
|---|---|---|
| I | Propylene glycol | 4.00 |
| J | Alcohol of agricultural origin 96% | 11.00 |
| J | Sol. Col. FDC blue N1 0.1% without preservative | 0.275 |
| J | Revitalizing PF TER G111 25975 | 0.3 |

The invention claimed is:

1. A cosmetic method for obtaining a slimming effect comprising:
providing a composition containing the association of a carob germ peptide extract (*Ceratonia siliqua* L.) and caffeine, or a derivative thereof, as a slimming active agent, and a physiologically acceptable medium, the physiologically acceptable medium comprising: dextran sulfate and rutin; and
topically applying the composition on at least a portion of the skin of the body or face;
wherein the carob germ peptide extract comprises between 1.5 g/l to 3.5 g/l of peptide compounds having a molecular weight below 5 kDa;
wherein the carob germ peptide extract and the caffeine are each present in a concentration of between 0.0001% and 20% of the total weight of the composition and are present in a ratio of total weight of the composition of caffeine to carob germ peptide extract of 1:1 to 1:1.33;
wherein the carob germ peptide extract and caffeine synergistically increases the expression of aquaglyceroporin 7.

2. The method according to claim 1, wherein topically applying comprises the application of an effective amount of the composition that increases lipolysis and promotes the elimination of lipids and the export of glycerol from the adipocytes.

3. The method according to claim 1, wherein topically applying comprises the application of an effective amount of the composition that reduces localized excess body fat.

4. The method according to claim 1, wherein topically applying comprises the application of an effective amount of the composition that attenuates an "orange peel" appearance of the skin.

5. The method according to claim 1, wherein the composition further comprises at least one additional active agent selected from the group consisting of vitamin A, retinoic acid, retinol, vitamin B3, vitamin B5, vitamin B6, vitamin B12, vitamin C, vitamin E, vitamin F, vitamin H, vitamin K, vitamin PP, coenzyme Q10, metalloproteinase inhibitors, amino acids, carnitine, carnosine, taurine, natural or synthetic peptides, plant-based peptides, yeast extracts, *Artemia Salina* extracts, phytosterols of synthetic or natural origin, salicylic acid, oligosaccharides, polysaccharides, amino sugars, polyphenols, flavonoids, lipids, phospholipids, cyclic AMP and derivatives thereof, adenylate cyclase enzyme activating agents, phosphodiesterase enzyme inhibiting agents, theophylline, theobromine, forskoline, esculin, ACE inhibitors, dioscorea extract, guarana extract, ivy extract, rockweed extract, algae extract, hydrolyzed *Prunella vulgaris* extract or elderberry extract.

6. The method according to claim 1, wherein the carob germ extract is present in a concentration of between 0.05% and 5% of the total weight of the composition.

7. The method according to claim 1, wherein caffeine, or a derivative thereof, is present in a concentration of between 0.05% and 5% of the total weight of the composition.

8. The method of claim 1, wherein the carob germ peptide extract is present as 2% of the total weight of the composition.

9. The method of claim 1, wherein topically applying the composition comprises a once or twice daily topical application.

10. The method of claim 9, wherein the once or twice daily topical application occurs for twelve days.

11. The method of claim 9, wherein the once or twice daily topical application occurs for 28 days.

12. The method of claim 1, wherein the caffeine derivative is a caffeine acid derivative or a caffeine salt.

13. The method of claim 12, wherein the caffeine salt is a caffeine carboxylate metal salt.

14. The method of claim 1, wherein the carob germ peptide extract has a polyphenol content that is less than 1% with respect to the dry weight of the peptide extract.

15. The method of claim 9, wherein the once or twice daily topical application occurs for one month.

16. The method of claim 1, wherein the dextran sulfate and rutin are present in a ratio of 10:1.

17. The method of claim 16, wherein the composition further comprises Na 4 EDTA.

18. The method of claim 1, wherein the composition further comprises Na 4 EDTA.

* * * * *